United States Patent [19]

Skotnicki et al.

[11] Patent Number: 4,692,517
[45] Date of Patent: Sep. 8, 1987

[54] C-3' ACYLAMINOOXY-7-[(2-AMINOTHIAZOL-4-YL)-α-(SUBSTITUTED-OXIMINO)ACETYL]-CEPHALOSPORIN DERIVATIVES

[75] Inventors: Jerauld S. Skotnicki, Chadds Ford; Thomas J. Commons, Wayne, both of Pa.

[73] Assignee: American Home Products Corporation, New York, N.Y.

[21] Appl. No.: 842,123

[22] Filed: Mar. 20, 1986

[51] Int. Cl.$^4$ .............................. C07D 501/34
[52] U.S. Cl. ................................. 540/222
[58] Field of Search ................. 540/222, 215

[56] References Cited

U.S. PATENT DOCUMENTS 4,465,831  8/1984  Bellani et al. .............. 540/222
4,489,072 12/1984  Sadaki et al. .............. 540/215

*Primary Examiner*—Donald G. Daus
*Assistant Examiner*—Barbara Cassatt
*Attorney, Agent, or Firm*—George Tarnowski

[57] ABSTRACT

There are disclosed novel antibacterial compounds having the formula

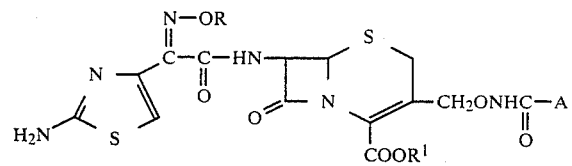

wherein
R is hydrogen, lower alkyl, lower alkenyl, lower alkynyl, cyclo lower alkyl, aryl of 6–12 carbon atoms, all the said foregoing groups being optionally substituted with carboxy, lower alkoxycarbonyl, phenoxycarbonyl, amino, mono- or di-lower alkyl substituted amino, hydroxy, lower alkoxy, phenoxy, carbamoyl, lower alkyl carbonyl, benzoyl, cyano, nitro, formamido, lower alkanoylamino or benzamido;
$R^1$ is hydrogen, lower alkyl or an alkali metal cation;
A is lower alkoxy, lower alkenoxy, lower alkynoxy, aryloxy of 6–12 carbon atoms, di-lower alkyl substituted amino, di-lower alkenyl substituted amino, di-lower alkynyl substituted amino, di-aryl of 6–12 carbon atoms substituted amino, lower alkyl, lower alkenyl, lower alkynyl, aryl of 6–12 carbon atoms.

2 Claims, No Drawings

C-3' ACYLAMINOOXY-7-[(2-AMINOTHIAZOL-4-YL)-α-(SUBSTITUTED-OXIMINO)ACETYL]CEPHALOSPORIN DERIVATIVES

The present invention is directed to C-3'-substituted cephalosporin derivatives having antibacterial activity. The compounds of the invention have the formula

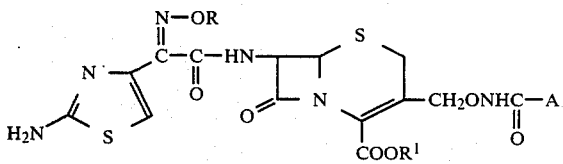

wherein

R is hydrogen, lower alkyl, lower alkenyl, lower alkynyl, cyclo lower alkyl, aryl of 6-12 carbon atoms, all the said foregoing groups being optionally substituted with carboxy, lower alkoxycarbonyl, phenoxycarbonyl, amino, mono- or di-lower alkyl substituted amino, hydroxy, lower alkoxy, phenoxy, carbamoyl, lower alkyl carbonyl, benzoyl, cyano, nitro, formamido, lower alkanoylamino or benzamido;

$R^1$ is hydrogen, lower alkyl or an alkali metal cation; and

A is lower alkoxy, lower alkenoxy, lower alkynoxy, aryloxy of 6-12 carbon atoms, di-lower alkyl substituted amino, di-lower alkenyl substituted amino, di-lower alkynyl substituted amino, di-aryl of 6-12 carbon atoms substituted amino, lower alkyl, lower alkenyl, lower alkynyl, aryl of 6-12 carbon atoms.

The terms "lower alkyl" and "lower alkoxy" refer to unbranched or branched moieties having 1-6 carbon atoms in the carbon chain. "Lower alkanoyl" refers to moieties having 1-6 carbon atoms in a carbon chain attached to a carbonyl group. The terms "lower alkenyl," "lower alkenoxy," "lower alkynyl" and "lower alkynoxy" refer to unbranched or branched moieties of the requisite degree of unsaturation having 2-6 carbon atoms in the carbon chain. The term "alkali metal cation" refers to $Na^+$ and $K^+$.

The compounds of the invention can be prepared by reacting a suitably protected cephalosporin derivative with a reactive species of the desired substituent A. The following reaction scheme, in which A is N-hydroxy-t-butylcarbamate, is representative of the preparative scheme in question:

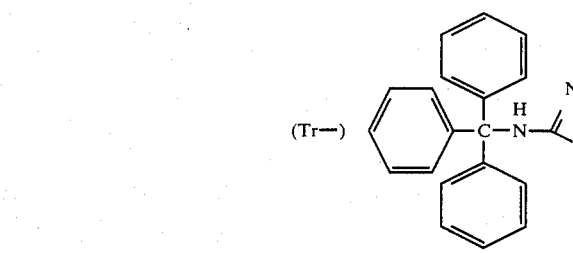

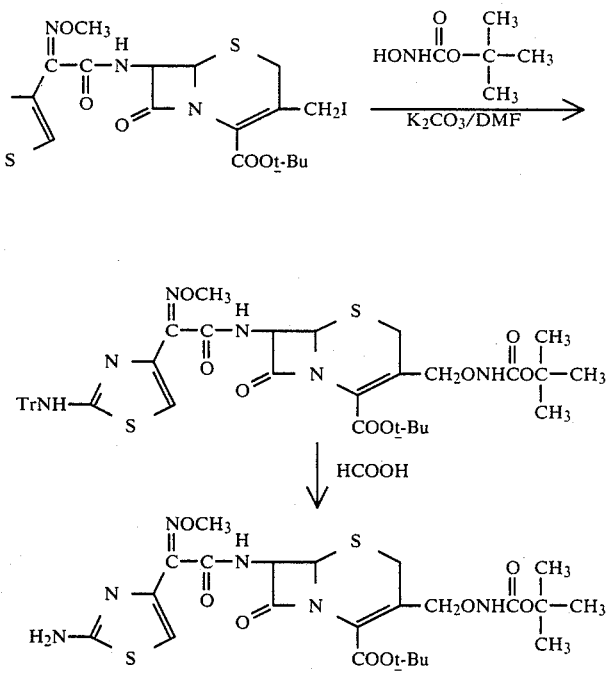

The initial reactive cephalosporin derivative has a suitably protected carboxyl group at the C-2' position and the amino group on the thiazole ring is also suitably protected. The protecting groups used include any readily displaceable groups known in the art for protecting primary amines and carboxylic acid groups. The exemplified protecting groups are triphenylmethyl (TR) and t-butyl, respectively, and these groups are preferred. In the above scheme, the triphenylmethyl group is displaced with formic acid leaving a primary amine group on the thiazole ring.

The starting cephalosporin derivative having the formula

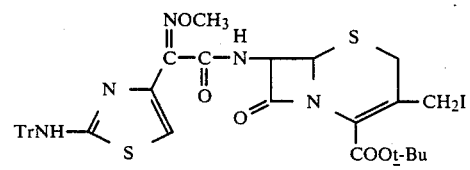

can be prepared according to the method described in Bonjouklian and Phillips, *Tetrahedron Letters*, 22, 3915 (1981). The A moieties are well-known in the art and are either commercially available or can be prepared by conventional methods.

The compounds of the invention are antibacterial agents effective against a variety of pathogenic Grampositive and Gram-negative bacterial organisms, including penicillin-resistant Staphylococcus. Thus, the antibacterial compounds of the invention are useful in the therapeutic treatment of bacterial infections in poultry and animals, including man, as well as being useful as nutritional supplements in animal feeds. The compounds of the invention are particularly active against the Gram negative bacteria and exhibit β-lactamase stability.

Because of their antibacterial properties, the compounds of the invention can be formulated into therapeutically valuable compositions comprising compounds of the invention and pharmacologically acceptable carriers. The latter term contemplates usual and customary substances employed to formulate solid, oral unit dosages for pharmacological purposes. The term also includes those substances employed to formulate either in unit dose or multidose form, oral and injectable suspensions and solutions, either directly or for reconstitution before administration.

To formulate dosages for administration according to this invention the compounds of the invention can be compounded into oral dosage forms such as tablets, capsules and the like. This is done by combining the compounds with conventional carriers, such as magnesium carbonate, magnesium stearate, talc, sugar, lactose, pectin, dextrin, starch, gelatin tragacanth, methylcellulose, sodium carboxymethylcellulose, low melting wax, cocoa butter, and the like. Diluents, flavoring agents, solubilizers, lubricants, suspending agents, binders, tablet-disintegrating agents and the like may be employed. The active ingredient may be encapsulated with or without other carriers. In all cases, the proportion of active ingredients in said compositions both solid and liquid will be at least sufficient to impart antibacterial activity thereto on oral administration.

The compounds may also be injected parenterally, in which case they are used in the form of a sterile solution containing other solutes, for example, enough saline or glucose to make the solution isotonic. The compounds may also be used topically and for this purpose they may be formulated in the form of dusting powders, solutions, creams or lotions in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter, the dosage is increased until the optimum effect under the circumstances is reached. In general, the compounds of the invention are most desirably administered at a concentration level that will generally afford effective results without causing any harmful or deleterious side effects.

The antibacterial activity of the compounds of the invention may be demonstrated by a standard pharmacological procedure which is described fully following the below presented examples directed to the preparation of the compounds useful in the invention.

PREPARATION OF STARTING CEPHALOSPORIN INTERMEDIATES (6R,7R)-3-(Iodomethyl)-7-[[(Z)-(methoxyimino)[2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester To a solution of 8.4 g (0.0111 mol) of (6R,7R)-3-acetoxymethyl-7-[[(Z)-methoxyimino)[2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester and 100 ml of $CH_2Cl_2$ at ambient temperature under a nitrogen atmosphere is added dropwise 3.35 ml (4.71 g/0.0235 mmol) of trimethylsilyl iodide. The reaction mixture is stirred for 2 hours, then washed successively with cold 10% $Na_2S_2O_3$ solution, saturated $NaHCO_3$ solution, and brine, dried over $Na_2SO_4$, and concentrated in vacuo. The multicomponent residue is purified by high performance liquid chromatography (2:98/EtOAc:$CH_2Cl_2$) to afford 3.62 g (40%) of the title compound: IR (KBr) 3280, 1785, 1715, 1675, 1520, 1365, 1300, 1150, and 1035 $cm^{-1}$; NMR ($CDCl_3$) 7.34 (s, 15H), 6.94–6.86 (m, 1H), 6.67 (s, 1H), 5.96–5.88 (m, 1H), 5.06 (d, 1H), 4.45 (d, 1H), 4.32 (d, 1H), 4.12 (s, 3H), 3.76 (d, 1H), 3.52 (d, 1H), 2.06 (s, 3H) and 1.56 (s, 9H).

EXAMPLE 1

(6R,7R)-7-[[(Z)-(2-amino-4-thiazolyl)(methoxyimino)acetyl]amino]-3-[[[[(1,1-dimethylethoxy)carbonyl]amino]oxy]methyl]-8-oxo-5-thia-1-azabicyclo[4.2.0]oct-2-ene-2-carboxylic acid 1,1-dimethylethyl ester

A.

(6R,7R)-3-[[[[(1,1-dimethylethoxy)carbonyl]amino]oxy]methyl]-7-[[(Z)-(methoxyimino)-[2-[(triphenylmethyl)amino]-4-thiazoyl]acetyl]amino]-8-oxo-5-thia-1-azabicyclo[4.2.0]oct-2-ene-2-carboxylic acid 1,1-dimethylethyl ester A mixture of 600 mg (0.73 mmol) of (6R,7R)-3-(iodomethyl)-7-[[(Z)(methoxyimino)[2-[(triphenylmethyl)amino]-4-thiazolyl]acetyl]amino]-8-oxo-5-thia-1-azabicyclo[4.2.0]oct-2-ene-2-carboxylic acid 1,1-dimethylethyl ester, 107 mg (0.8 mmol) of N-hydroxy-t-butylcarbamate, 111 mg (0.8 mmol) of $K_2CO_3$ and 4 ml of anhydrous dimethylformamide is stirred at ambient temperature for 3 hours. The reaction mixture is diluted with ethyl acetate and washed copiously with water, then brine, and dried over $Na_2SO_4$. The solvent is removed under reduced pressure to give a waxy solid. Trituration with ether affords 275 mg (46%) of the title compound: IR (KBr) 3380, 1785, 1720, 1670, 1525, 1370, 1155 and 1040 $cm^{-1}$; NMR (DMSO-$d_6$) δ 9.68–9.50 (m, 2H, enchangeable), 8.86 (br-s, 1H, exchangeable), 7.44–7.2 (m, 15H), 6.74 (s, 1H), 6.8–6.62 (m, 1H), 5.12 (d,1H), 4.62 (d, 1H), 4.38 (d, 1H), 3.82 (s, 3H), 3.84–3.3 (complex m, 2H, partially obscured by $H_2O$), 1.46 (s, 9H) and 1.39 (s, 9H); FAB-MS m/e 827 (M+H).

B.

(6R,7R)-7-[[(Z)-(2-amino-4-thiazolyl)(methoxyimino)acetyl]amino]-3-[[[[(1,1-dimethylethoxy)carbonyl]amino]oxy]methyl]-8-oxo-5-thia-1-azabicyclo[4.2.0]oct-2-ene-2-carboxylic acid 1,1-dimethylethyl ester A solution of 250 mg (0.3 mmol) of A. above and 3 ml of HCOOH (88%) is stirred at ambient temperature for 3 hours, then filtered. The filtrate is concentrated in vacuo to give a waxy solid. Trituration with ether furnishes (145 mg (82%) of title compound: IR (KBr) 3320 (br), 3180 (br), 1780, 1715 (br), 1670 (br), 1525, 1365, 1150 and 1030 cm$^{-1}$; NMR (DMSO-d$_6$) δ 9.74–9.56 (m, 1H, exchangeable), 7.38–7.12 (m, 3H, exchangeable), 5.88–5.74 (m, 1H), 5.24–5.12 (m, 1H), 5.04 (d, 1H), 4.74 (d, 1H), 3.86 (s, 3H), 3.64–3.24 (complex m, 2H), and 1.48 (br-Δ, 18H); FAB-MS m/e 585 (M+H).

EXAMPLE 2

The compounds of the invention are tested for their antibacterial activity. The test is carried out as follows:

The organisms used in the test comprise the following:

*Staphylococcus aureus* (penicillin-sensitive and resistant), *Pseudomonas aeruginosa, Escherichia coli, Salmonella pneumoniae, Bordetella bronchiseptica, Proteus vulgaris, P. mirabilis, Acinetobacter calcoaceticus.*

Test organisms may be added or deleted in order to reflect current clinical patterns of antibiotic susceptibility or shifts in pathogenic potential.

Organisms are normally grown for 18 hours in Brain Heart Infusion at 35° C. Cultures are adjusted with saline to MacFarland No. 1.5 standard prior to use.

Stock concentrations (e.g. 2,500 μg or units per ml) are prepared in a suitable vehicle. Two-fold dilutions are made. One ml quantities of each dilution are incorporated in 9 ml of the appropriate agar (e.g. Seed) in sterile Petri plates. The hardened surface is inoculated with test organisms by use of a Steers replicating device. The plates are incubated (e.g. 18 hours at 35° C.) and activity is determined.

The least amount of material that completely inhibits the test organisms is the Minimal Inhibitory Concentration (MIC), which is expressed in μg or units per ml.

A compound of the invention, when tested according to the above outlined procedures, gives the results summarized in Table 1.

TABLE 1

| Organism | Compound of Example 1B MIC (μg/ml) |
|---|---|
| *Staphylococcus aureus* ATCC 29213 | 64 |
| *Streptococcus faecalis* ATCC 29212 | 128 |
| *Enterobacter cloacae* ATCC 13047 | 32 |
| *Escherichia coli* ATCC 25922 | 4 |
| *Klebsiella pneunomiae* KL-1 | 1 |
| *Proteus vulgaris* A 84354 1 | 1 |
| *Pseudomonas aeruginosa* ATCC 27853 | 128 |
| *Serratia marcescens* ATCC 13880 | 16 |

The results show that the compound tested has antibacterial activity against the organisms used in the test procedures, in particular against Gram-negative organisms.

What is claimed is:

1. A compound having the formula

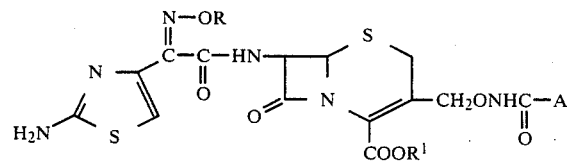

wherein
R is hydrogen, lower alkyl, or cyclo lower alkyl, the said foregoing groups being optionally substituted with carboxy or lower alkoxycarbonyl;
R$^1$ is hydrogen, lower alkyl or an alkali metal cation; and
A is lower alkoxy or aryloxy of 6–10 carbon atoms.

2. The compound of claim 1, having the name (6R,7R)-7-[[(Z)-(2-amino-4-thiazolyl)(methoxyimino)acetyl]amino]-3-[[[[(1,1-dimethylethoxy)carbonyl]amino]oxy]methyl]-8-oxo-5-thia-1-azabicyclo[4.2.0]oct-2-ene-2-carboxylic acid 1,1-dimethylethyl ester.

* * * * *